(12) United States Patent
Webler et al.

(10) Patent No.: US 7,594,903 B2
(45) Date of Patent: Sep. 29, 2009

(54) CONTROLLING SHAFT BENDING MOMENT AND WHIPPING IN A TENDON DEFLECTION OR OTHER TENDON SYSTEM

(75) Inventors: William Earl Webler, Escondido, CA (US); Robert Hayzelden, Canyon Lake, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 99 days.

(21) Appl. No.: 10/255,034

(22) Filed: Sep. 25, 2002

(65) Prior Publication Data

US 2004/0059288 A1   Mar. 25, 2004

(51) Int. Cl.
*A61M 31/00* (2006.01)

(52) U.S. Cl. .................................. 604/95.04

(58) Field of Classification Search ... 604/95.01–95.04, 604/93.01, 528–532, 264, 523, 533; 600/146, 600/147, 149, 150, 434; 607/115–120
See application file for complete search history.

(56) References Cited

U.S. PATENT DOCUMENTS

| | | | |
|---|---|---|---|
| 4,838,859 A | | 6/1989 | Strassmann |
| 5,254,088 A | | 10/1993 | Lundquist et al. |
| 5,462,527 A | | 10/1995 | Stevens-Wright et al. |
| 5,507,725 A | * | 4/1996 | Savage et al. ............ 604/95.04 |
| 5,549,542 A | * | 8/1996 | Kovalcheck ................. 600/146 |
| 5,571,085 A | | 11/1996 | Accisano, III |
| 5,676,653 A | * | 10/1997 | Taylor et al. ............. 604/95.04 |
| 5,715,832 A | * | 2/1998 | Koblish et al. ............... 600/564 |
| 5,820,591 A | * | 10/1998 | Thompson et al. ........ 604/95.01 |
| 5,944,690 A | * | 8/1999 | Falwell et al. .......... 604/170.03 |
| 5,954,654 A | * | 9/1999 | Eaton et al. .................. 600/462 |
| 6,123,699 A | | 9/2000 | Webster, Jr. |
| 6,171,277 B1 | * | 1/2001 | Ponzi ...................... 604/95.04 |
| 6,183,463 B1 | * | 2/2001 | Webster, Jr. ................. 604/528 |
| 6,416,510 B1 | * | 7/2002 | Altman et al. ................ 606/41 |
| 6,522,933 B2 | * | 2/2003 | Nguyen ...................... 607/116 |
| 6,547,787 B1 | * | 4/2003 | Altman et al. ................ 606/41 |
| 6,569,114 B2 | * | 5/2003 | Ponzi et al. .............. 604/95.04 |
| 6,663,588 B2 | * | 12/2003 | DuBois et al. ........... 604/95.04 |
| 2001/0037084 A1 | | 11/2001 | Nardeo |
| 2002/0065485 A1 | | 5/2002 | DuBois et al. |
| 2002/0068868 A1 | | 6/2002 | Thompson et al. |
| 2002/0177766 A1 | * | 11/2002 | Mogul ........................ 600/374 |
| 2003/0109778 A1 | * | 6/2003 | Rashidi ...................... 600/374 |

OTHER PUBLICATIONS

PCT International Search Report for PCT Appln No. US03/25454, mailed Dec. 5, 2003 (6 pages).

* cited by examiner

*Primary Examiner*—Matthew F Desanto
(74) *Attorney, Agent, or Firm*—Blakely Sokoloff Taylor & Zafman LLP

(57) ABSTRACT

A tendon deflection system including a shaft, a plurality of tendons movably disposed within the shaft, and a force-balancing element coupled to the tendons. In a first section, the plurality of tendons are arranged around the shaft at equal angles to each other and at an equal distance from the center of the shaft. The tendons operating in concert with the force-balancing element minimize the moment expressed in the first section. The second section is deflectable and includes at least one tendon, extending from the plurality of tendons in the first section, which is arranged along one side of the shaft such that the bending moment expressed in the second section is greater than the first section.

14 Claims, 19 Drawing Sheets

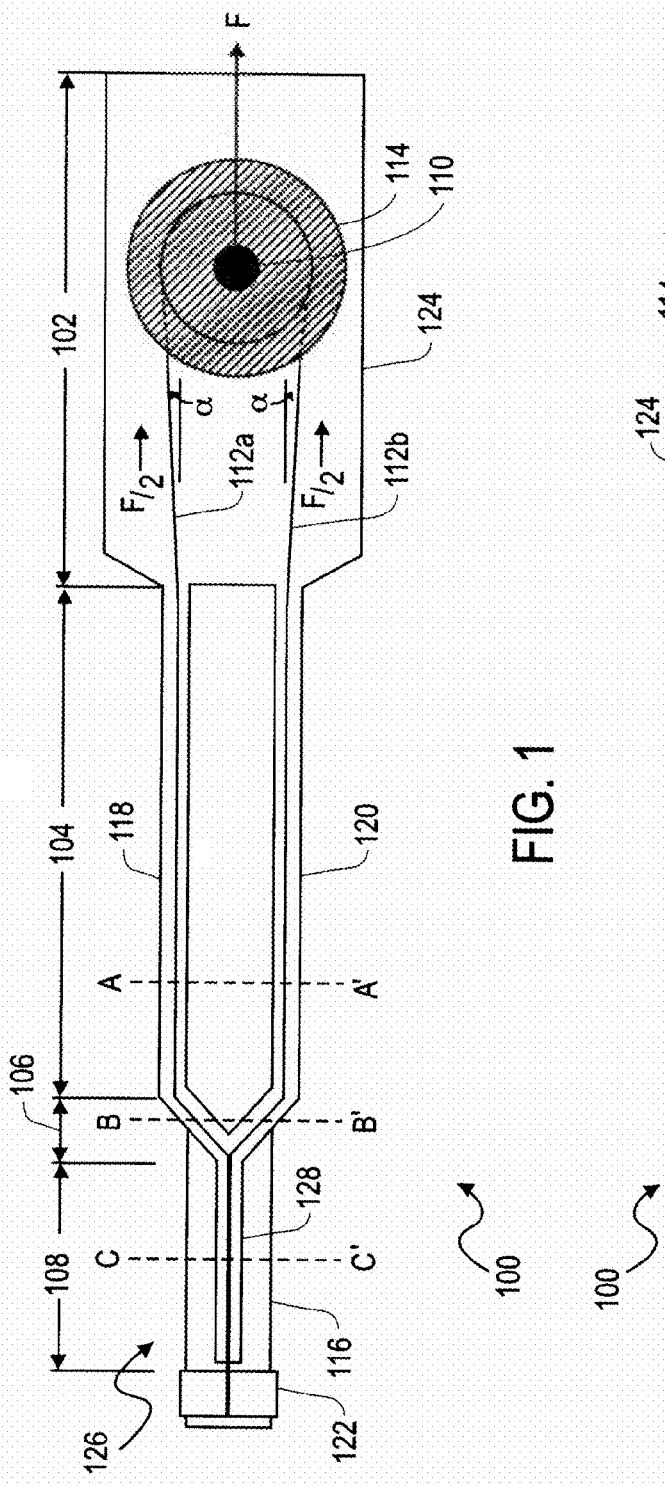
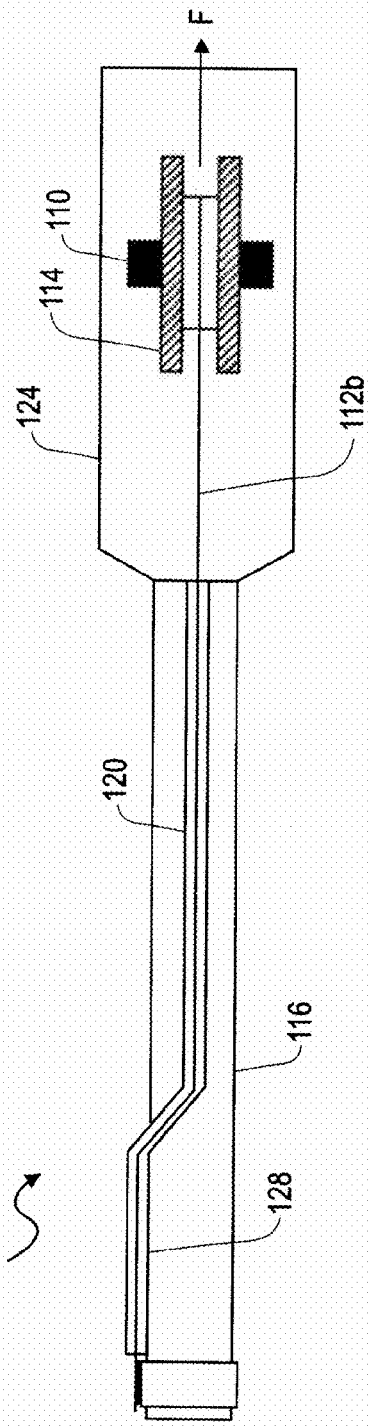
FIG. 1
FIG. 2

CONTROLLING SHAFT BENDING MOMENT AND WHIPPING IN A TENDON DEFLECTION OR OTHER TENDON SYSTEM

FIELD

The embodiments disclosed herein relate generally to a tendon deflection system, and more particularly to controlling shaft bending moment and "whipping" in a deflectable catheter.

BACKGROUND

Tendon deflection systems such as catheters have been in common use in medical practice for many years. The catheters are used to probe locations inside a body lumen that are otherwise unreachable without surgery. A catheter is inserted into a major vein or artery, or other body lumen that is near the body surface, possibly with the aid of an introducer entering the body lumen and a guide catheter previously inserted.

The catheter is then guided to the area of concern by inserting the catheter further into the body lumen. As medical knowledge increases, catheterizations have become more complicated and exacting. In many situations the ability to control the position and orientation of the catheter tip may largely determine the usefulness of the catheter.

Flexible catheters having deflectable (steerable) tips are also known. Such a catheter generally has a control handle at its proximal end for controlling deflection of the tip in one or more directions. The catheter may also include a puller wire or tendon that extends coaxially (on axis) through an elongated reinforced catheter body and then off axis in a deflectable distal tip portion.

The tendon may be anchored or fixedly attached at or distal to the deflectable tip portion by welding, soldering, brazing, adhesive or other means of attachment to a structure (e.g., electrode or other metal anchor) coupled to the catheter shaft. However, each of these methods of attachment has drawbacks.

For example, welding can weaken and/or melt the wire. In addition, welding deforms the wire, which creates a smaller cross-sectional area in the deformed portion relative to the non-deformed portion. Necessarily, the deformed portion with the smaller cross-sectional area is the weakest part of the wire. Thus, the weakest point of the wire is disadvantageously located at the point of attachment.

Soldering and brazing require the use of flux to facilitate the fusion of the wire to the metal anchor coupled to the catheter shaft. This is problematic since flux is often acidic and, if not thoroughly cleaned from the catheter, will corrode the wire and the bond. In addition, flux tends to discolor the metal (e.g., gives stainless steel a rusted appearance), which makes it difficult to ascertain whether the catheter is sterile before inserting the catheter into a patient's body.

Finally, it is difficult to create an effective bond between metals with an adhesive. Thus, the current techniques of attaching the tendon to the distal portion of the catheter shaft are not acceptable.

Regardless of the method of attachment used, tension on the tendon (made with longitudinal movement of the proximal portion of the tendon) relative to the catheter body or shaft results in the generation of a bending moment in the deflectable tip portion, which causes the catheter tip portion to deflect. The more proximal portions of the catheter body tend not to deflect because the tendon extends coaxially (on axis) within the shaft and, therefore, little bending moment is generated.

The above design operates well in catheters where the work elements of the catheter or catheter system do not materially affect the radial symmetry of the catheter body's flexural modulus, such as in electrophysiology ("EP") catheters. In an EP catheter, the electrical wires running through the catheter body are very flexible and, if a strain is relieved, have little influence on the catheter body's flexural modulus (e.g., stiffness). However, in catheters or catheter systems with less flexible work elements, the work elements must occupy the axial position within the catheter body and not the tendon.

If the less flexible work element were placed in an off-axis position in the catheter body, the catheter body would have a preferred rotational orientation when rotated within a curved conduit (e.g., within the aorta or at the exit to the introducer sheath). This lack of flexural modulus radial symmetry introduces a phenomenon known as "whipping", where the ability to control the exact position and orientation of the catheter tip is compromised.

Whipping occurs when the distal end of the catheter does not follow the rotation applied to the catheter on the proximal end in a smooth and continuous manner. Thus, whipping is undesirable in catheter systems where the curved or deflected distal end of the catheter must be rotated to direct the distal end towards a desired structure or the curved end of the catheter must sweep through a desired arc in a controlled manner to perform a desired function.

Two examples of catheters with less flexible work elements are guide catheters and needle catheters. In a guide catheter, or a catheter system including a guide catheter, the less flexible work element is the catheter or device that is delivered and positioned through the inner diameter ("ID") of the device. In a needle catheter, the less flexible work element is the hollow shaft that provides the injection conduit to the needle and/or the means to advance or retract that needle.

There are several problems with placing the tendon off-axis in the catheter body of such devices. One of the problems is that all portions of the shaft proximal to the anchor point are subjected to the bending moment generated by the tension force on the tendon. One undesirable consequence of the bending moment being expressed in all sections of the catheter shaft proximal to the anchor point during deflection is that these sections become curved to some extent and, thus, have a preferred rotational orientation (lowest energy state) when confined in a curved conduit (e.g., the aorta or at the exit to the introducer sheath), which can cause whipping.

Rotation of the catheter is yet another concern since rotation affects the path length of the tendon. For example, the tendon path length is decreased in rotational positions where the tendon is rotated toward the inside of a conduit curve. Thus, if the tendon's proximal end is held in a fixed position relative to the catheter (typical case) and/or the force applied to the tendon decreases in response to the tendon path length decreasing, the deflection of the tip of the catheter decreases. The decrease in deflection returns energy to the catheter, causing the distal tip to rotate more rapidly than the proximal end.

Conversely, in the rotational positions where the tendon is rotated toward the outside of a conduit curve, the path length is increased. Thus, the tension on the tendon increases, which causes the deflection of the catheter tip to increase as well. This removes energy from the catheter, causing the distal tip to rotate more slowly than the proximal end. This disadvantageously increases the chances of undesired whipping.

Similar problems also occur in tendon systems in which the tension on a tendon (or tendons) is used to perform other functions. One example of such a system is minimally invasive surgical (MIS) devices. During MIS procedures, the surgeon performs surgery through small punctures or incisions using endoscopic devices to guide the manipulation of specialized tools (work devices) which are at or near the distal end of shafts.

The use of a small puncture or incision significantly decreases patient risk, trauma and recovery time when compared to conventional surgery. The specialized tools may include cutting devices, like scissors, biopsy retrieval devices and suturing devices that may be activated by a tendon that is controlled by the surgeon at or near the shaft's proximal end. Another tendon (or tendons) may also be provided for deflection to aid in the positioning of the distal end of the specialized tool by the surgeon.

SUMMARY

Various tendon deflection systems are disclosed herein. One embodiment includes a shaft having a wall and a lumen defined by the shaft, a plurality of tendons movably disposed within at least one of the wall and the lumen, and a force-balancing element. At least one of the plurality of tendons has a distal portion coupled to the shaft or to a work device coupled to the shaft. A force-balancing element is coupled to the plurality of tendons such that when force is exerted on the force-balancing element, the force-balancing element exerts a balanced force on the plurality of tendons to operate the shaft. As used herein, operation of the shaft refers to at least one of deflecting a deflectable portion of the shaft and actuating a work device coupled to the shaft.

In various embodiments, the plurality of tendons in a proximal portion of the shaft are arranged around the shaft at an equal angle from each other and at an equal distance from the center of the shaft. Such a configuration, taken together with the balanced force exerted on each tendon by the force-balancing element, minimizes the moment experienced by the proximal portion of the shaft. Thus, the combination of the force-balancing element and the tendon configuration described above allows the proximal portion of the shaft to remain relatively straight while (i) a portion of the shaft is deflected, or (ii) a work device coupled to the shaft is actuated.

In embodiments having a deflectable portion of the shaft, the tendon(s) in the deflectable portion of the shaft are disposed along one side of the shaft. Thus, the resultant bending moment experienced by the deflectable portion of the shaft is substantially higher than the bending moment in the proximal portion of the shaft, which allows deflection of the deflectable portion of the shaft while the proximal portion remains relatively straight. In various embodiments, the plurality of tendons may be arranged in deflectable portions to allow for deflection in multiple directions and/or at controlled relative magnitudes.

In embodiments having a work device coupled to the shaft, at least one of the plurality of tendons is coupled to the work device to control the work device. Various embodiments may include a configuration of the tendons to permit both work device control and deflection control.

The various embodiments advantageously lower the "whipping" effect discussed above (caused by tendon path length changes) and prevent unwanted alteration of the work device's state of actuation, both of which can be caused by rotation of the shaft within a curved conduit or body cavity.

DESCRIPTION OF THE DRAWINGS

Various embodiments are illustrated by way of example and not by way of limitation in the figures of the accompanying drawings in which like references indicate similar elements. It should be noted that references to "an," "one," or "various" embodiments in this disclosure are not necessarily to the same embodiment, and such references mean at least one.

FIG. 1 illustrates a top view of one embodiment of a tendon deflection system.

FIG. 2 illustrates a side view of the tendon deflection system of FIG. 1.

DETAILED DESCRIPTION

Figure 3:
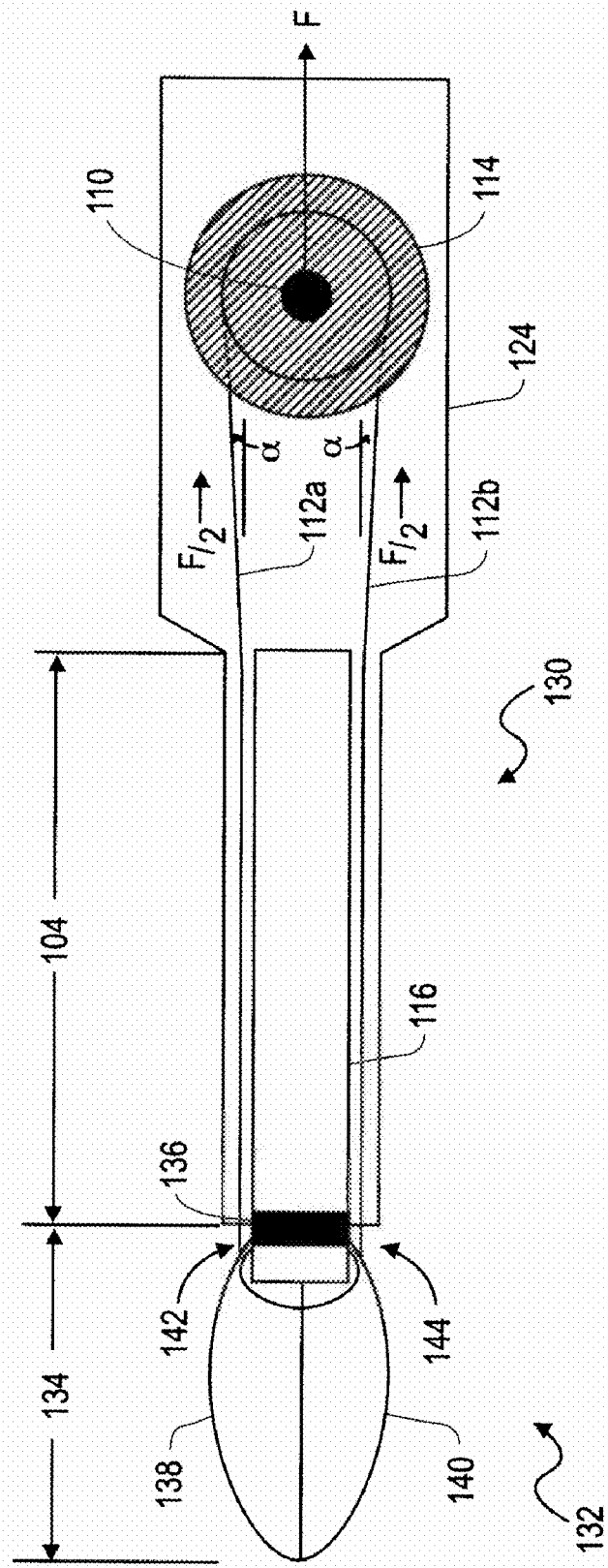
FIG. 3 illustrates a top view of one embodiment of a tendon system with a work performing device.

In the following description, for the purposes of explanation, numerous specific details are set forth in order to provide a thorough understanding of the various embodiments. It will be apparent to one skilled in the art that the embodiments may be practiced without some of these specific details.

The following description and the accompanying drawings provide examples for the purposes of illustration. However, these examples should not be construed in a limiting sense as they are not intended to provide an exhaustive list of all possible implementations. In other instances, certain structures and devices are omitted or simplified in order to avoid obscuring the details of the various embodiments.

FIGS. 1 and 2 illustrate top and side views, respectively, of one embodiment of tendon deflection system 100. In the illustrated embodiment, tendon deflection system 100 comprises a plurality of sections 102, 104, 106, 108. Some sections are enclosed within or attached to shaft 116. Each section 102, 104, 106, 108 may be configured to apply an appropriate amount of force to tendon 112 (comprised of sections 112a and 112b). Furthermore, tendon 112 may be displaced from the center of shaft 116 by a predetermined distance to provide an appropriate moment to shaft 116. Sections 104, 106, 108 may be coupled in any particular combination. Tendon deflection system 100 may also include other elements, not shown in FIG. 1 or 2, such as guidewires, other catheters, needle shafts, luers, other lumens, forceps, and scissors, as well as other similar devices.

In section 102, tendon 112 is looped around pulley 114 at proximal end 124 of tendon deflection system 100. To deflect distal end 126 of system 100, a force F (or displacement) is applied to pivot center 110 of pulley 114, while proximal end 124 of tendon deflection system 100 is held in a fixed position. Thus, a substantially equal tension force of F/2 is produced on each of tendon sections 112a and 112b. However, when the tension forces on tendon sections 112a and 112b are not equal, pulley 114 rotates to bring the tension forces back into balance. Although the illustrated embodiment uses pulley 114, pulley 114 may be replaced with any other element(s) that provide balanced forces on tendon sections 112a and 112b.

Further, in some embodiments, the effects of angle α on the tension forces experienced by tendon 112 may need to be accounted for when configuring tendon deflection system 100. Although these additional tension forces may be small when angle α is small, the forces need to be accounted for in a precise system. Guides, pulleys, and/or other devices may be added to control angle α so that the additional forces associated with angle α approach zero.

In section 104 of tendon deflection system 100, each section of tendon 112 is contained within tendon sheath 118 and tendon sheath 120, respectively. Tendon sheaths 118 and 120 are positioned 180° apart on the outer diameter of shaft 116.

Figure 4:
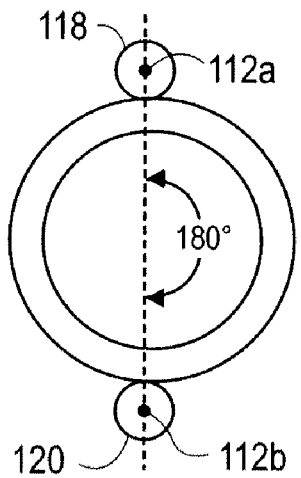
FIG. 4 illustrates a cross-sectional view of an embodiment of tendon sheaths within section 104 of the tendon deflection system of FIG. 1.

FIG. 4 illustrates a cross-sectional view of an embodiment of tendon sheaths within section 104 of tendon deflection system 100. Hence, FIG. 4 shows a cross section A-A' in section 104 shown in FIG. 1.

Figure 5:
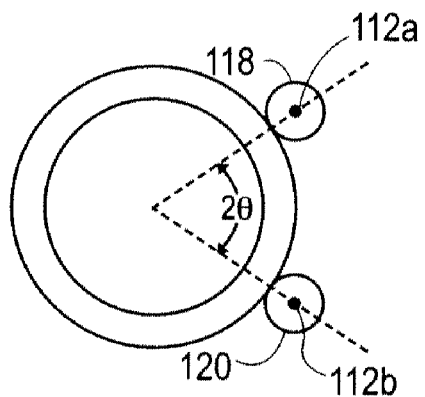
FIG. 5 illustrates a cross-sectional view of an embodiment of tendon sheaths within section 106 of the tendon deflection system of FIG. 1.

Section 106 is an intermediate portion of shaft 116 in which tendon sheaths 118, 120 are positioned at an angle 2θ from each other. The angle 2θ may vary between 0° and 180°. Accordingly, tendon sheaths 118 and 120 move together on the outer diameter of shaft 116 toward each other, such that ends of tendon 112 enter into single tendon sheath 128 in section 108. FIG. 5 illustrates a cross-sectional view of an embodiment of tendon sheaths 118 and 120 within section 106 of tendon deflection system 100. Hence, FIG. 5 shows a cross section B-B' in section 106 shown in FIG. 1.

Figure 6:
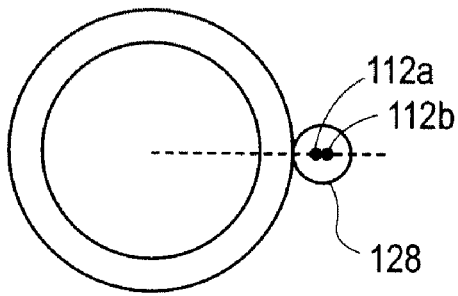
FIG. 6 illustrates a cross-sectional view of an embodiment of tendon sheaths within section 108 of the tendon deflection system of FIG. 1.

FIG. 6 illustrates a cross-sectional view of an embodiment of tendon sheath 128 within section 108 of tendon deflection system 100. Hence, FIG. 6 shows a cross section C-C' in section 108 shown in FIG. 1. In FIG. 1, two ends of tendon 112 exit the distal end of tendon sheath 128 and are attached to anchor ring 122. Anchor ring 122 is fixedly attached to distal end 126 of tendon deflection system 100.

Figure 29:
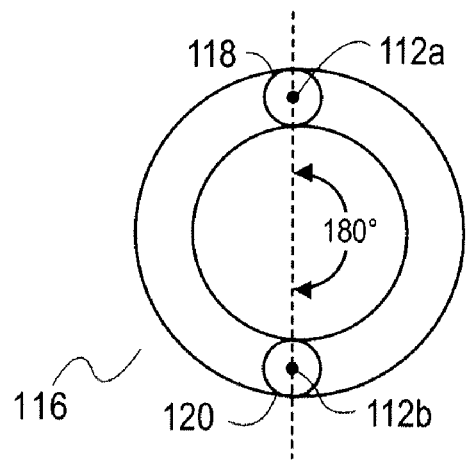
FIG. 29 illustrates a cross-sectional view of a proximal portion of a tendon deflection system wherein the tendon sheaths are disposed within the shaft wall.
Figure 30:
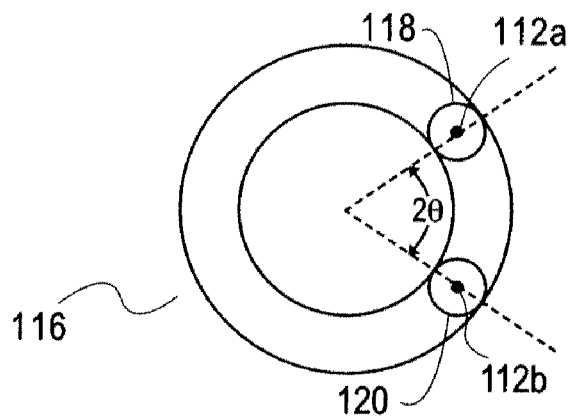
FIG. 30 illustrates a cross-sectional view of an intermediate portion of the tendon deflection system of FIG. 29.
Figure 31:
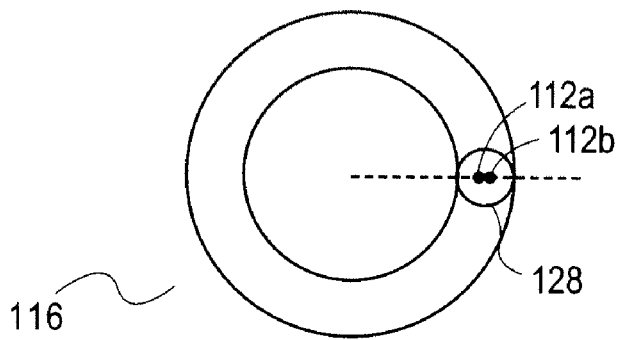
FIG. 31 illustrates a cross-sectional view of a distal portion of the tendon deflection system of FIG. 29.

In some embodiments, tendon 112 and sheaths 118 and 120, 128 are embedded in the wall of or within shaft 116, as shown in FIGS. 29 through 31. Furthermore, for manufacturing purposes, it may be more practical to have two tendons 112 that are individually wrapped around pulley 114 in the directions as shown in FIG. 1. Proximal ends of tendon 112 may then be secured to pulley 114.

Alternatively, proximal ends of two tendons 112 may be joined to each other and looped around pulley 114. In another alternative embodiment, tendon 112 may simply be looped around pulley 114, with no distinct ends coupled to pulley 114 or to each other. In yet another alternative, tendon 112 may be a single continuous loop that loops around pulley 114, runs the length of the catheter, and is coupled in some manner to the distal end of the catheter to facilitate deflection of the deflectable catheter tip.

Thus, as used herein, the term "tendon" refers to a length of tendon material, regardless of whether different sections of tendon material are part of the same tendon or are part of different tendons. Furthermore, when a tendon is "coupled" to a structure, it is understood that, among other methods of attachment, the term "coupled" also encompasses attaching a loop of the tendon to the structure.

Figure 7:
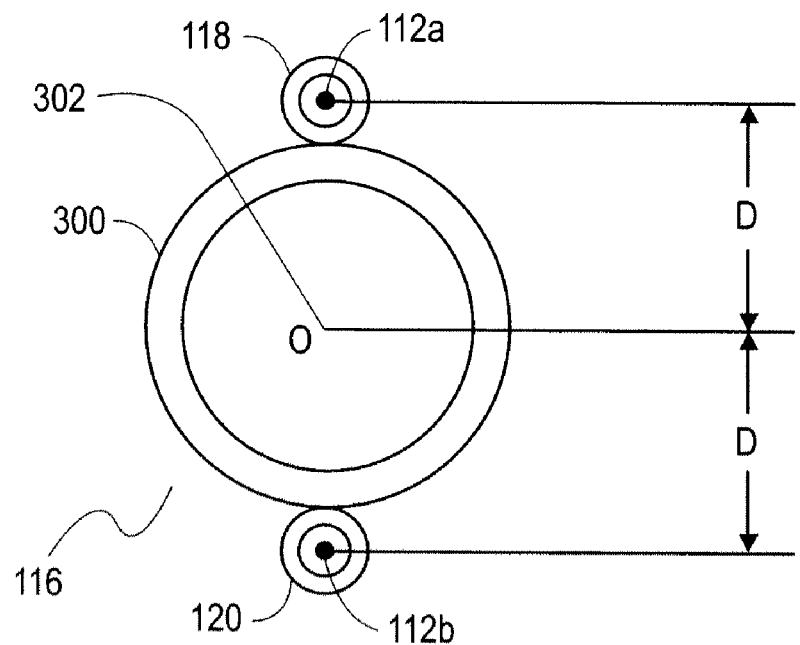
FIG. 7 illustrates a detailed cross-sectional view (A-A') of an embodiment of the tendon wire and sheaths within section 104 of the tendon deflection system of FIG. 1.
Figure 8:
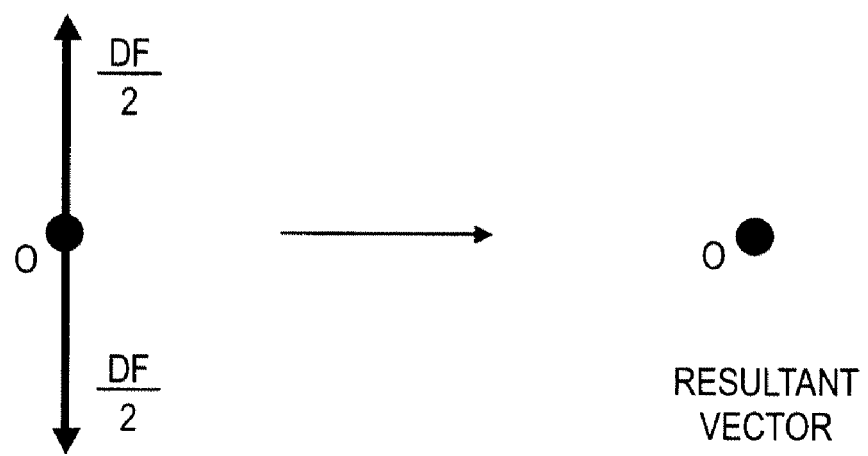
FIG. 8 illustrates a moment vector analysis of the forces acting on the tendon deflection system of FIG. 7.

FIG. 7 illustrates a detailed cross-sectional view (A-A') of an embodiment of tendon 112 and sheaths 118 and 120 within section 104 of tendon deflection system 100 shown in FIG. 1. In the illustrated embodiment, tendon 112 and sheaths 118 and 120 are disposed on outer diameter 300 of shaft 116. Tendon sections 112a and 112b are 180° apart from each other, as described above. Each section of tendon 112 is a distance D from center 302 of shaft 116. The bending moment created by a tendon (or tendon section) not only has a magnitude, but also has a direction and, therefore, may be expressed as a vector. To simplify and better illustrate the following discussions, the direction of this vector may be defined as the direction from the center of the shaft cross-section to the center of the tendon (which is also the direction of the center of the induced radius of curvature). The magnitude of the moment vector is the product of the tendon tension force (F/2 on each side) times the distance (D) of tendon 112 from center 302 of shaft 116. Hence, the moment may be expressed as follows:

$$M = \frac{DF}{2}[\cos\theta + \cos(\theta + 180)] \quad (1)$$

$$= \frac{DF}{2}[\cos\theta - \cos\theta] = 0$$

where θ is the angle of the vector from any arbitrary reference line. Thus, in section 104 of FIG. 1, each end of tendon 112 produces a moment with amplitude of DF/2, as illustrated in FIG. 8. However, the moments applied to shaft 116 in section 104 cancel out because the directions of these moments are 180° apart from each other. Therefore, the resultant moment vector applied to section 104 of tendon deflection system 100 is approximately zero, as shown in FIG. 8. Accordingly, with low or zero applied moment, section 104 produces almost no deflection in response to increases in the applied force F. Further, little or no deflection in section 104 significantly reduces whipping caused by tendon-induced shaft curvature. In an actual shaft design, tolerances, clearances and manufacturing variances may cause some small residual moment to be applied to section 104 of shaft 116.

The total path length of tendon 112 in section 104 remains constant during rotation within a curved conduit because tendon sheaths 118 and 120 are oriented 180° from each other. When one side of the path length of tendon 112 is lengthened, the other side is shortened by the same amount. Pulley 114 rotates to feed more of tendon 112 to the lengthening path and to retract tendon 112 from the shortening path. Since the total path length of tendon 112 remains constant during rotation, the force F and the deflections of other sections of system 100 (or the device actuation state of system 130) remain unchanged. This very effectively minimizes the tendon-induced whipping in response to catheter rotation within a curved conduit, as has been previously described. If pulley 114 is constrained from rotating, the difference in tendon path length on each side of pulley 114 would cause the forces on each side of pulley 114 to be unequal, which can cause "whipping," as described above. This causes pulley 114 to rotate on its pivot center 110 back into balance as soon as pulley 114 is released.

Tendon induced whipping may also be minimized, but not eliminated, by spiraling the tendon around the shaft. However, to minimize whipping, the pitch of this spiral (i.e., the tightness of the spiral) must be several times smaller than the arc length of the anticipated curved conduit in which the shaft is confined in order for the configuration to be effective. Since the arc length and curvature of the curved conduit are variable (e.g., due to anatomy variations), a "net curve" shaft section may be formed.

A "net curve" shaft section is the section of the conduit confined curved shaft section whose net moment is not zero (or the degree to which the tendon path length is not constant with shaft rotation) over the arc length of the curved conduit. A short spiral pitch (a "tight spiral") provides a short maximum "net curve" shaft section length that may create this preferred rotational orientation or whipping effect.

However, a tight spiral results in increased friction. In a tight spiral, the tendon tension forces are directed more toward the surface of the tendon sheath, which raises the friction forces between the surface and the tendon. This makes pulling the tendon more difficult (e.g., requires more force to pull the tendon) and, thus, makes creating and controlling the desired deflection more difficult.

Moreover, additional force on the tendon may also mean that the cross-section of the tendon must be increased to withstand the extra load on the tendon to avoid breaking or permanently deforming the tendon (e.g., wire) or its attachments and/or to avoid excessive tendon elastic extension. Also, the increased friction, combined with the increasing deformation of the tendon as the tendon negotiates the spiral path, makes the manufacturing step of inserting the tendon into its sheath significantly more difficult.

Another disadvantage of a tight spiral is that the spiral may significantly increase the length of the tendon. The longer tendon produces more elastic deformation, which may require a longer "throw" (e.g., must translate the proximal end of the tendon a longer distance to create the same bending moment or deflection) for the deflection control device. Hence, a tight spiral design may increase shaft size and may make it harder to achieve an efficient deflection control device.

Furthermore, a tight spiral directs more of the tendon's tension force to produce a torque on that section of the shaft. The increasing tendon tension force, to cause increasing deflection, must increase the torsion applied to the shaft created by the tendon's spiral. This effectively causes the distal tip of the shaft to rotate during deflection and decreases the operator's ability to control the tip's rotational orientation. This effect may be minimized by judiciously changing the direction of the spiral.

For instance, assuming consistent shaft torsion properties and spiral pitch, if one half the length of the spiral was in the clockwise direction and the other half in the counter-clockwise direction, the shaft would rotate equally in the clockwise and counter-clockwise directions. Thus the net rotation present at the distal tip would be zero during deflection manipulation. However, manufacturing variances, tolerances, clearances and other imperfections may likely result in some net rotation, but that rotation may be effectively minimized. Additionally, frequent spiral direction changes may reduce the effects of shaft inconsistencies and inconsistencies in the environment in which the shaft is placed.

Besides elimination of whipping, it is desirable to have a section of the catheter (e.g., a catheter body) remain relatively straight while the tip is deflected. This generally requires that the section have a high flexural modulus (e.g., high stiffness). However, a high flexural modulus in the catheter shaft may not be desirable because the catheter must negotiate curves within the body lumen.

Alternatively, the tendon could be spiraled around the catheter shaft, as described above, to keep the section relatively straight. However, an undesirable consequence of spiraling the tendon around the catheter shaft is that the catheter assumes a corkscrew configuration during tip deflection, which shortens the effective length of the catheter. This is problematic since the catheter length in a spiral configuration may be shortened significantly more than that for a configuration where the catheter is only subjected to the compressive forces applied by the tendon during deflection.

For example, the amount of catheter shortening due to compression alone varies roughly in proportion to the amount of tip deflection. Thus, the shortening due to spiraling further complicates tip position control beyond merely compensating for shortening due to compression. As previously described in discussions of section 104, the resultant bending moment applied to section 104 is minimized. Therefore, section 104 may be constructed with a lower flexural modulus and remain relatively straight.

Thus, the spiraling of the tendon to minimize whipping and maintain a relatively straight shaft section may not be a satisfactory solution by itself. However, in a section of catheter designed with a cross-section like that of section 104 (tendons 180° apart), spiraling both tendons may be incorporated to further minimize the effects of any residual moment due to construction inconsistencies or tolerances. With little resultant applied moment, there will be little spiral deformation and a reduced effect of any "net curve."

Figure 32:
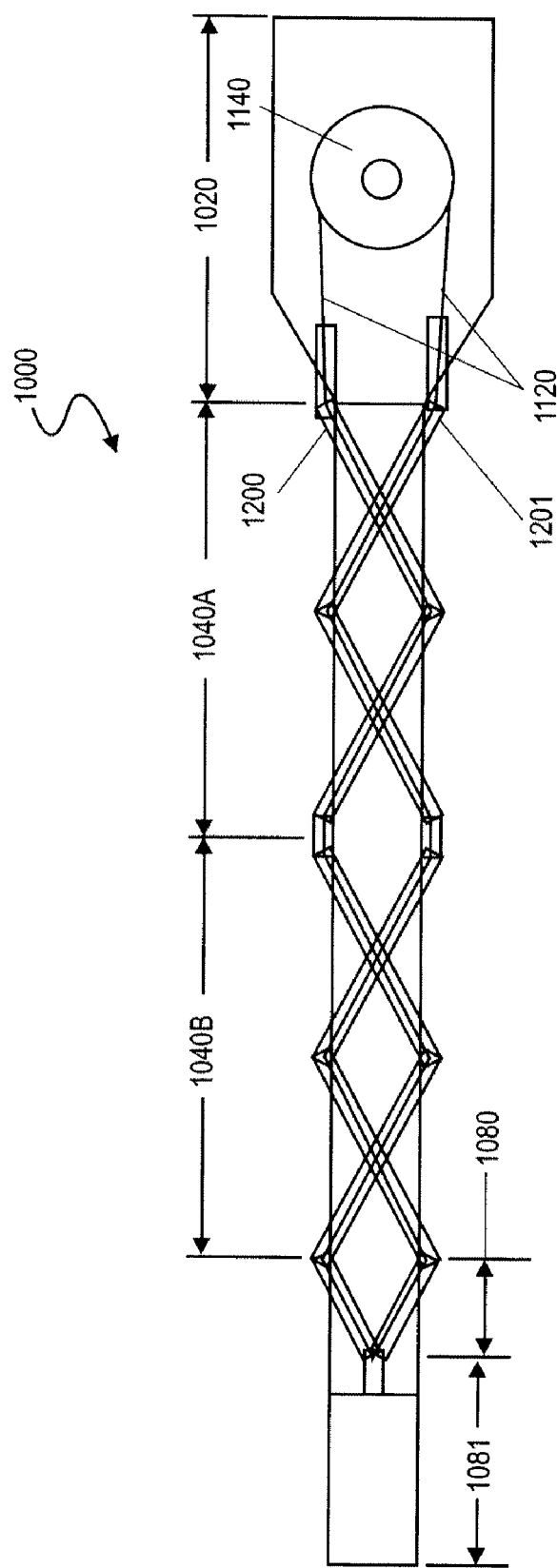
FIG. 32 illustrates a side view of an embodiment of a tendon deflection system with a tendon spiraled around a section of the system.

FIG. 32 shows a side view of an embodiment of a tendon deflection system where a tendon is wrapped around at least a section of the system. FIG. 32 shows tendon deflection system 1000 including section 1020, section 1040A, section 1040B, section 1080, and section 1081. Tendon deflection system 1000 includes sheath 1200 and sheath 1201 with the two ends of tendon 1120 in each sheath, respectively. The two ends of tendon 1120 spiral in one direction around shaft section 1040A and spiral in the other direction around shaft section 1040B. In section 1040A and section 1040B, the two ends of tendon 1120 are approximately 180° away from each other on the shaft section. Section 1080 is a shaft section where two ends of tendon 1120 are brought together. Section 1081 includes work element (e.g., a cutter) or the deflecting portion of the tendon deflection system. Tendon 1120 is looped around pulley 1140 in section 1020.

FIG. 32 shows a side view of an embodiment of a tendon deflection system where a tendon is wrapped around at least a section of the system. FIG. 32 shows tendon deflection system 1000 including section 1020, section 1040A, section 1040B, section 1080, and section 1081. Tendon deflection system 1000 includes sheath 1200 and sheath 1201 with the two ends of tendon 1120 in each sheath, respectively. The two ends of tendon 1120 spiral in one direction around shaft section 1040A and spiral in the other direction around shaft section 1040B Section 1080 is a shaft section where two ends of tendon 1120 are brought together. Section 1081 includes a deflecting portion of the tendon deflection system. In section 1020, tendon 1120 is looped around pulley 1140.

Returning now to the figures, FIG. 3 shows one embodiment of work device actuation tendon system 130. FIG. 3 is similar to FIGS. 1 and 2, except that the portions distal to section 104 have been replaced with work performing device section 134. For purposes of illustration, work device section 134 is chosen to contain cutting device 132. However, any work device, including surgical devices, could be used.

Cutting device 132 is comprised of mounting ring 136 and jaws 138, 140. Cutting device 132 is attached to shaft 116 by ring 136. Tendon sections 112a and 112b are attached to proximal portions 142 and 144 of jaws 138 and 140, respectively. Proximal portions 142 and 144 bias jaws 138 and 140 closed, as shown, with an appropriate amount of force to facilitate cutting. Also, proximal portions 142 and 144 are elastically deformable with approximately equal elastic properties, such that, when subjected to an adequate level of the equal tension forces F/2 applied by tendon sections 112a and 112b, jaws 138 and 140 open approximately equally. Thus, by applying and removing a force or displacement to pivot center 110 of pulley 114, jaws 138 and 140 of cutting device 132 may be opened and closed to cut tissue with appropriate manipulation of system 130.

The previous discussions of FIG. 1 in regards to moment minimization, whipping, tendon path length and the balancing of tendon section (or tendon) forces apply to FIG. 3. Thus, the rotational orientation of the cutting plane of jaws 138 and 140 may be more precisely controlled when shaft section 104 is confined in a curved conduit or body cavity. Additionally, because individual path length changes of the tendon ends are compensated for by the rotation of pulley 114 during the rotation of tendon system 130, the position of jaws 138 and 140 remain unchanged (e.g., device actuation state is unchanged).

Figure 9:
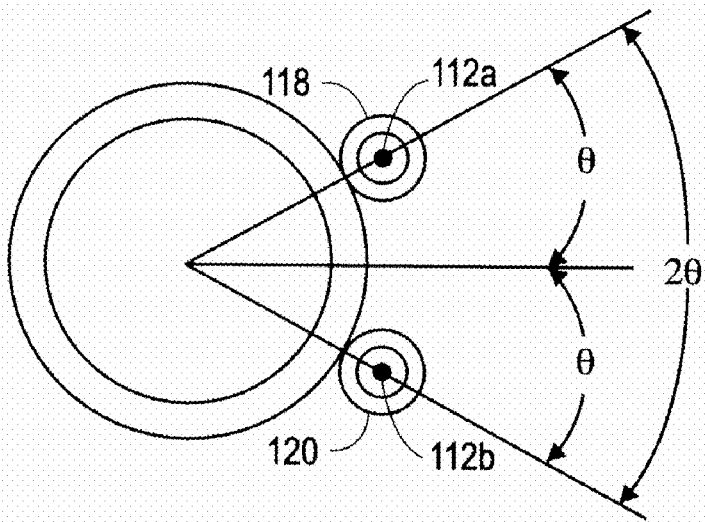
FIG. 9 illustrates a detailed cross-sectional view (B-B') of an embodiment of the tendon wire and sheaths within section 106 of the tendon deflection system of FIG. 1.

FIG. 9 illustrates a detailed cross-sectional view (B-B') of an embodiment of tendon sections 112a and 112b and sheaths 118 and 120 within section 106 of tendon deflection system 100 shown in FIG. 1. In the illustrated embodiment, tendon sections 112a and 112b are separated by an angle 20. Angle 20 in section 106 is variable depending upon where along the length of section 106 the cross-section is taken.

Figure 10:
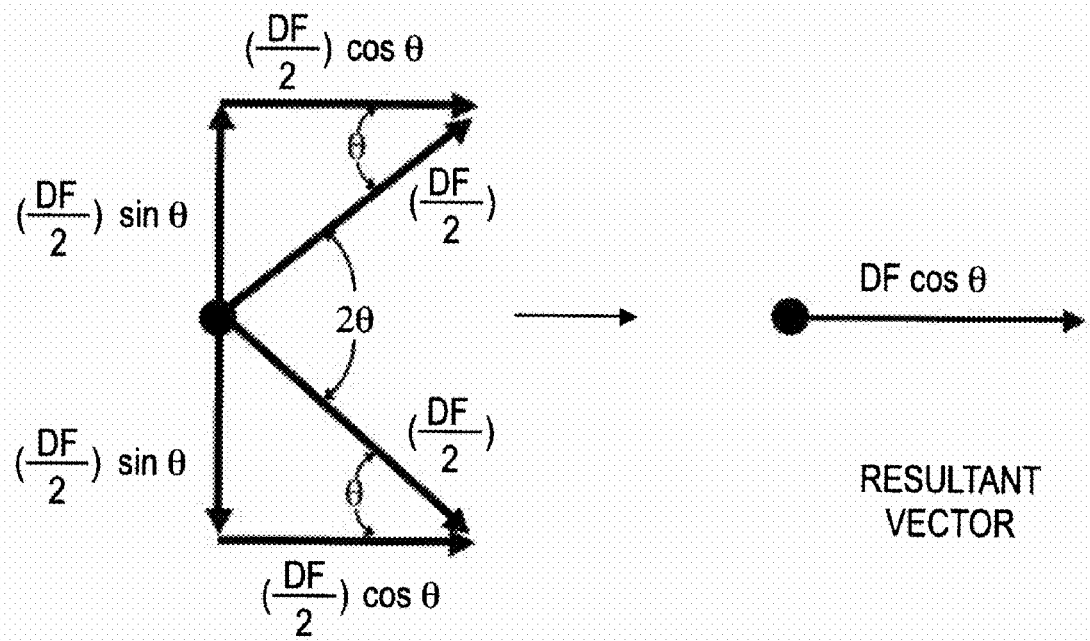
FIG. 10 illustrates a moment vector analysis of the forces acting on the tendon deflection system of FIG. 9.

FIG. 10 indicates that the angle that separates the moment vectors of each section of tendon 112 (each with a magnitude of DF/2) is the same angle that separates tendon sections 112a and 112b (2θ). Moreover, the resultant moment is applied in the direction of the line that bisects that angle (2θ≦180°). As shown in FIG. 10, the two component vectors of the tendon moments with an amplitude of (DF/2)cosθ are in the same direction and, therefore, add to become (DF)cosθ. The two vertical component vectors with amplitude of (DF/2)sinθ are in opposite directions and, therefore, cancel each other out. Hence, the resultant moment may be expressed as follows:

$$M = \frac{DF}{2}\cos\theta + \frac{DF}{2}\cos\theta = DF\cos\theta \quad (2)$$

Accordingly, the amplitude of the applied or resultant moment is equal to DF times the cosine of one half the angle that separates the vectors.

Equation (2) is also valid for the configuration shown in FIGS. 7 and 8. For that configuration, 2θ=180°, so θ=90. Therefore, $$M=DF \cos \theta=DF \cos (90)=DF(0)=0 \quad (3)$$

Further, Equation (2) is valid for the configuration of section 108 shown in FIGS. 1 and 6. In that configuration, θ becomes small, and cosθ approaches a value of one. Therefore, the resultant applied moment approaches a value of DF. If tendon sections 112a and 112b are joined to a second tendon in section 108, then θ equals zero and the applied moment is calculated as follows:

$$M=DF \cos \theta=DF \cos (0)=DF(1)=DF \quad (4)$$

Thus, by adjusting the angle "2θ" between tendon sections 112a and 112b, the percentage of the maximum available resultant moment (DF) that is expressed in a particular section along the length of shaft 116 may be chosen. In one embodiment, this percentage may be predicted as 100 times cosθ. Additionally, the direction that bisects angle "2θ" predicts the direction of deflection. Thus, by adjusting the positions of the ends of the tendon 112 relative to shaft 116, the direction of deflection may also be chosen.

Figure 11:
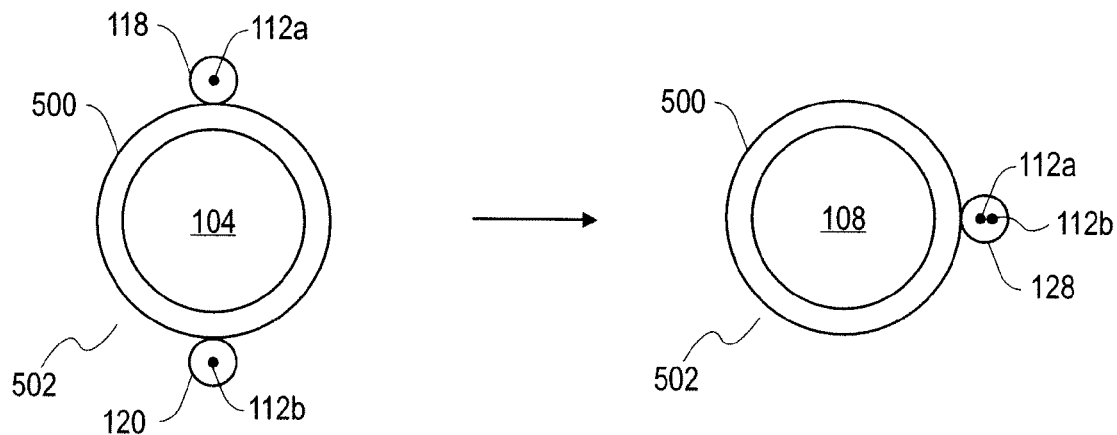
FIG. 11 shows one embodiment of the tendon and sheaths in sections 104 and 108 of the tendon deflection system of FIG. 1.

FIG. 11 shows the configurations of tendon 112 and sheaths 118, 120, and 128 in sections 104 (e.g., left cross-sectional view) and 108 (e.g., right cross-sectional view) of FIG. 1, respectively. The left cross-sectional view of tendon 112 and sheaths 118 and 120 illustrates cross-section A-A' in section 104. Moreover, the right cross-sectional view of tendon 112 and sheath 128 illustrates cross-section C-C' in section 108.

FIG. 11 shows that tendon sheaths 118, 120, and 128 are disposed on outer diameter 500 of shaft 502. The right cross-sectional view of FIG. 11 shows that tendon sections 112a and 112b are both disposed in tendon sheath 128 in section 108 of FIG. 1. Furthermore, the view on the right indicates that tendon sections 112a and 112b, in this embodiment, move side by side in tendon sheath 128.

Figure 12:
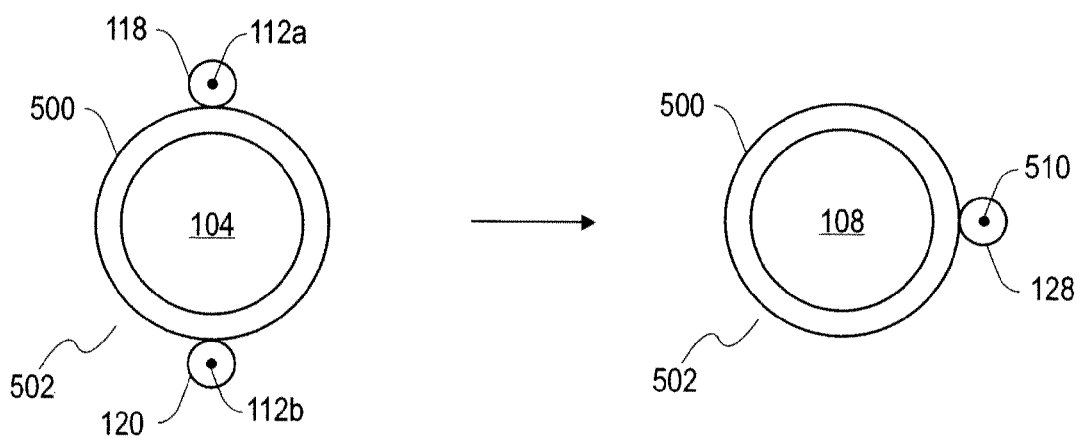
FIG. 12 shows another embodiment of the tendon and sheaths in sections 104 and 108 of the tendon deflection system of FIG. 1.

In some embodiments of the shaft design, it may be more advantageous to sever ends of tendon 112 just distal to section 106, and to join the ends with single tendon 510, as shown in FIG. 12. Single tendon 510 may then traverse the length of section 108 and be attached to anchor ring 122. However, tendon 510 may be attached to shaft 502, in any practical manner, distal to the portions of shaft 502 for which a deflection is desired.

Figure 13:
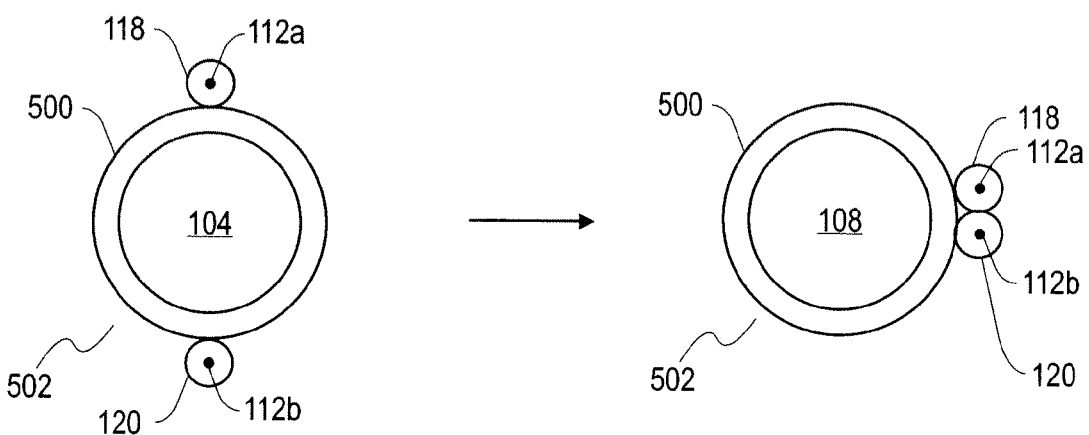
FIG. 13 shows a further embodiment of the tendon and sheaths in sections 104 and 108 of the tendon deflection system of FIG. 1.

In other embodiments, it may be more practical to continue tendon sheaths 118 and 120 side by side through section 108, and to eliminate the need for tendon sheath 128, as shown in FIG. 13. The elimination of tendon sheath 128 also eliminates the need to join tendon sheaths 118, 120 together.

In various embodiments, tendon 112 may be made of metal, metal alloys or other materials with suitable physical properties. For example, tendon 112 may be made of material with suitable tensile properties such as Vectran, Kevlar, and the like.

FIGS. 22 through 27 show various embodiments of attaching a loop of a tendon to an anchor element disposed on the distal tip of a catheter. In various embodiments, the anchor element is an electrode tip. The electrode tip advantageously acts as an anchor for the tendon and as an electrode to pick up electrical input and relay the electrical current via the tendon to, for example, an instrument coupled to the tendon.

Although not shown, if a location system sensor is also disposed near the distal tip of the catheter, the tendon can also carry an electrical signal from the sensor. The tendon can carry the electrical signals for both the electrode tip and the sensor as long as the signals are isolated (e.g., use different references and/or operate in different frequency ranges).

Although not shown in the figures, the same principles described in regards to the electrode tips of FIGS. 22 through 27 may be applied to other anchoring devices (e.g., anchor ring 122 of FIG. 1) to effectively deflect a portion of a catheter by increasing the tension on the tendon, which is looped around a portion of the electrode tip.

Figure 22:
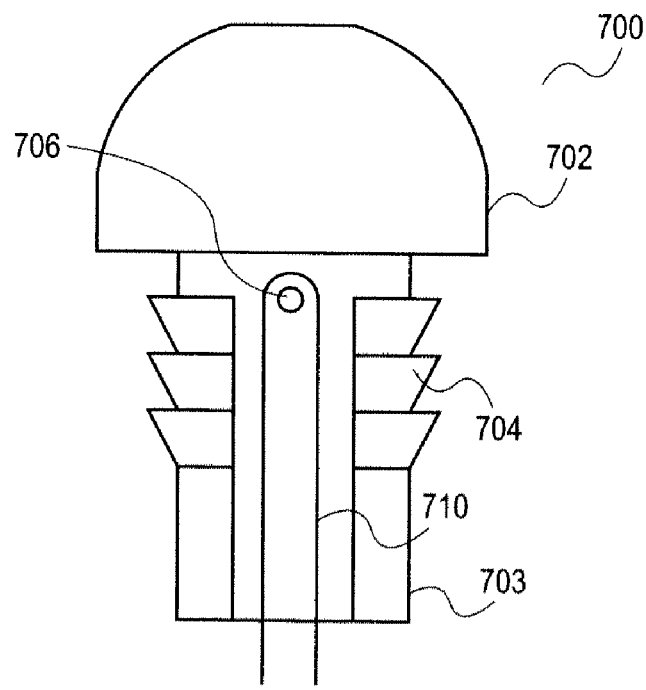
FIG. 22 is a side view of an embodiment of an electrode tip with a tendon looped around a peg protruding from the main body portion of the electrode tip.

Focusing first on FIG. 22, electrode tip 700 has top portion 702 and main body portion 703. Main body portion 703 further includes protrusion 706. Protrusion 706 may have any size or shape so long as a loop of tendon 710 can be disposed around protrusion 706. Once a loop of tendon 710 is disposed around protrusion 706, a holding element (not shown) is placed around at least main body portion 703 to engage electrode tip 700 and tendon 710 in order to prevent the loop of tendon 710 from disengaging from main body portion 703.

In various embodiments, the holding element may be a ring, similar to anchor ring 122 of FIG. 1. Thus, the holding element ring would snugly slide over main body portion 703 to effect a press fit over barbs 704 of main body portion 703. A press fit of this nature would simultaneously crush the sheath material of the catheter into barbs 704 and effectively engage the loop of tendon 710. Alternatively, the holding element ring could be crimped around main body portion 703 rather than sliding the holding element ring around main body portion 703.

Figure 23:
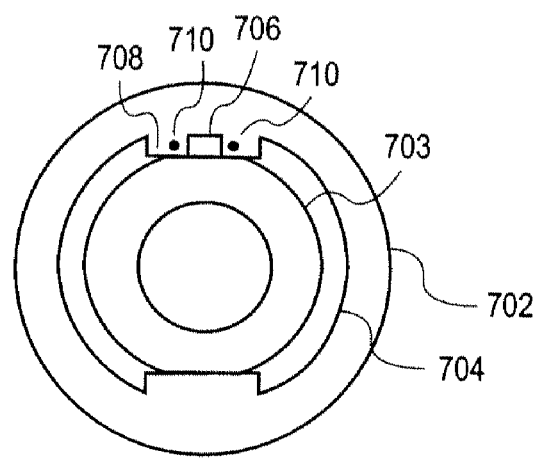
FIG. 23 is a bottom view of the electrode tip shown in FIG. 22.

FIG. 23 is a bottom view of electrode tip 700 of FIG. 22. Longitudinal channel 708 formed in main body portion 703 provides an area where tendon 710 may rest against main body portion 703 such that once the holding element is placed over main body portion 703, tendon 710 is not smashed into barbs 704.

Figure 24:
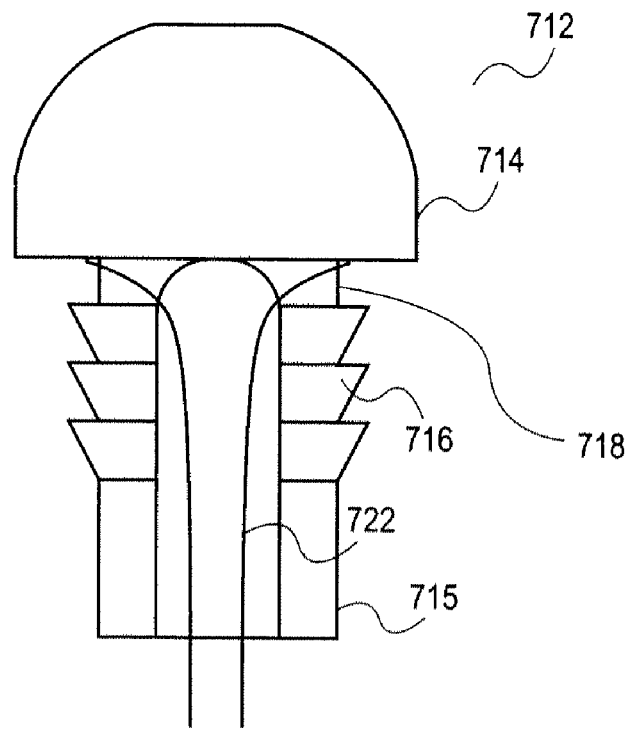
FIG. 24 is a side view of an embodiment of an electrode tip with a tendon loop disposed within an annular channel formed in the main body portion of the electrode tip.
Figure 25:
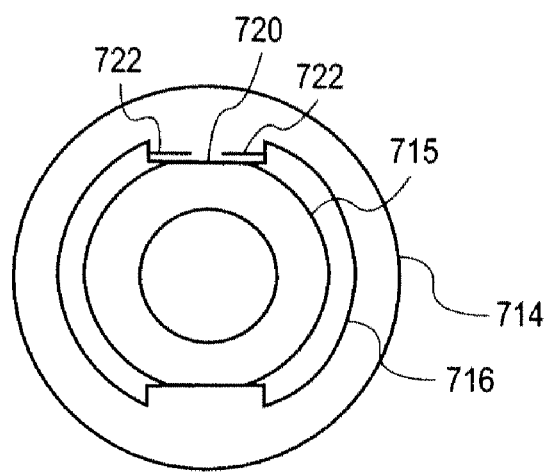
FIG. 25 is a bottom view of the electrode tip shown in FIG. 24.

FIG. 24 is another embodiment of the electrode tip. Electrode tip 712 of FIG. 24 includes top portion 714 and main body portion 715. Similar to electrode tip 700 of FIG. 22, electrode tip 712 includes barbs 716 and channel 720 (see FIG. 25, which is a bottom view of FIG. 24). However, instead of a protrusion from main body portion 715, tendon 722 is looped around channel 718 formed in main body portion 715. Once tendon 722 is looped within channel 718, a holding element, as described above, can be disposed around main body portion 715 to prevent tendon 722 from disengaging from main body portion 715.

Figure 26:
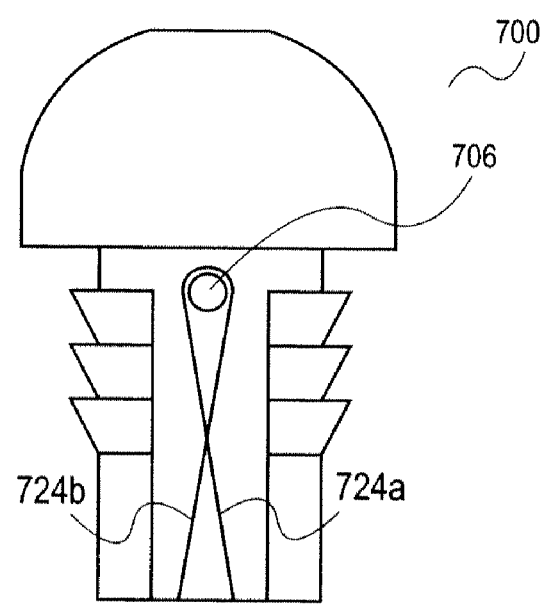
FIG. 26 is a side view of an embodiment of an electrode tip with a tendon looped around a peg protruding from the main body portion of the electrode tip such that the tendon sections are crossed.
Figure 27:
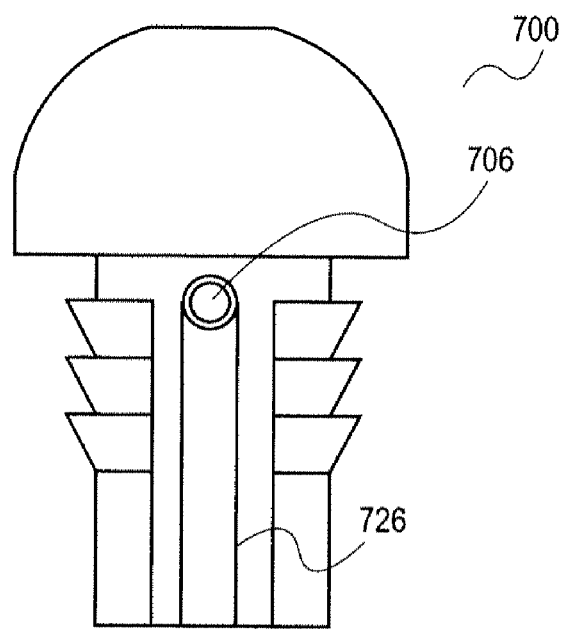
FIG. 27 is a side view of an embodiment of an electrode tip with a tendon looped around a peg protruding from the main body portion of the electrode tip such that the loop completely encircles the peg.

FIGS. 26 and 27 show alternative tendon loop configurations around electrode tip 700. FIG. 26 shows tendon sections 724a and 724b crossed below the point at which the loop of tendon 724 engages protrusion 706. FIG. 27 shows tendon 726 looped around the entire circumference of protrusion 706.

Figure 28:
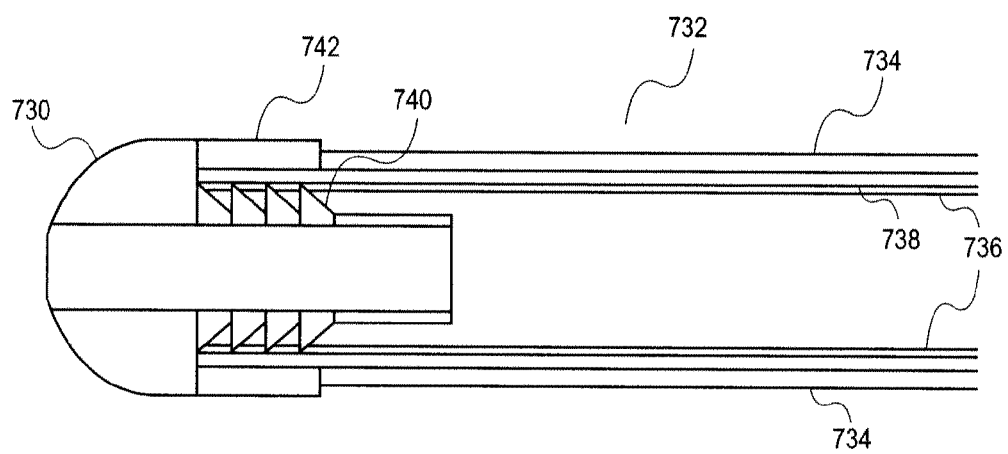
FIG. 28 is a cross-sectional view of an alternative method of attaching a tendon to an electrode tip.

FIG. 28 shows a cross-sectional view of an alternative method of attaching a tendon to an electrode tip. Specifically, electrode tip 730 is disposed at the distal end of catheter 732. Although other components are omitted to simplify the figure, catheter 732 comprises outer jacket material 734 and shaft liner 736.

Tendon 738 is disposed between outer jacket material 734 and shaft liner 736. Tendon 738 and shaft liner 736 are captured between barbs 740 of electrode 730 and outer ring 742 in order to couple tendon 738 to electrode tip 730. In other embodiments, outer jacket material 734 is also captured between barbs 740 and outer ring 742. In addition, tendon 738 may be disposed within a sheath (not shown). If a tendon sheath is used, tendon 738 may have the sheath removed in the "capture area" between barbs 740 and outer ring 742, or the sheath may also be disposed within the capture area.

The method of attachment shown in FIG. 28 may be used in conjunction with any of the other principles disclosed herein. For example, multiple tendon sections may be attached to the electrode tip. If desired, the tendon sections may be located at equal angles from each other (e.g., 180° apart for two tendons, 120° apart for three tendons, etc.). Alternatively, the tendons could be stacked as shown in FIG. 11 or may be placed side-by-side as in FIG. 13; in either of these embodiments, the tendons would still be captured between an outer ring and the barbs of an electrode tip.

Although the embodiments of tendon deflection system 100 and device actuation tendon system 130 have been described generally with tendon 112 having two ends, tendon deflection systems may be configured with more than two tendon sections (or more than two tendons) and still gain the above-described benefits. For example, in the embodiment of tendon deflection system 600 shown in FIGS. 14 through 16, the expressed moment may be minimized, as described above in conjunction with FIGS. 1 through 13, where tendons 602, 604, 606 are spaced at equal angles (θ) within shaft wall 610 and at an equal distance from shaft center 612. This configuration produces balanced (and equal) forces applied to each tendon 602, 604, 606. A tendon deflection system with an even number (e.g., 2, 4, 6, . . . ) of tendons may balance forces using a plurality of moment-balancing elements, such as pulleys or levers.

Figures 15, 16:
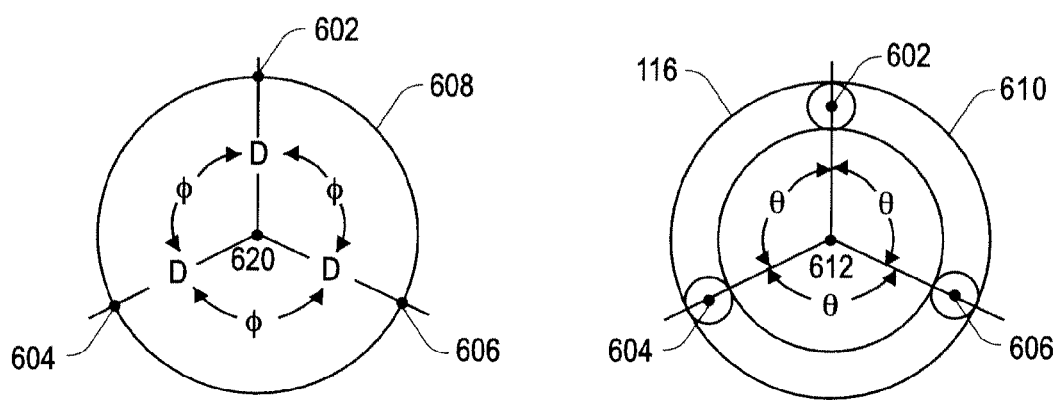
FIG. 15 shows a cross-sectional view of an embodiment of the tendon system of FIG. 14.
FIG. 16 shows an embodiment of the force-balancing element of FIG. 14.

FIG. 16 shows a front view of an embodiment of element 608 (e.g., a disc) that balances the forces acting on tendons 602, 604, 606. Proximal ends of tendons 602, 604, 606 are attached to element 608 at an equal distance (D) away from the point of applied force (F) or translation 620 (e.g., the center of element 608), and at an equal angle φ around the point of applied force 620. Also, the point of applied force 620 is configured to align with center 612 of shaft 116 (see FIG. 16), such that the configuration allows element 608 to provide sufficient translation and pivot movement.

Furthermore, the size of element 608 (or distance (D)) should be sufficient to accommodate the expected individual tendon (or tendon section) path length changes. Furthermore, this configuration also keeps the total tendon path length constant and, therefore, minimizes tendon induced whipping (and device actuation, if applicable). As tendon system 600 is rotated with shaft 116 confined in a curved conduit, element 608 pivots at center 620.

Figure 14:
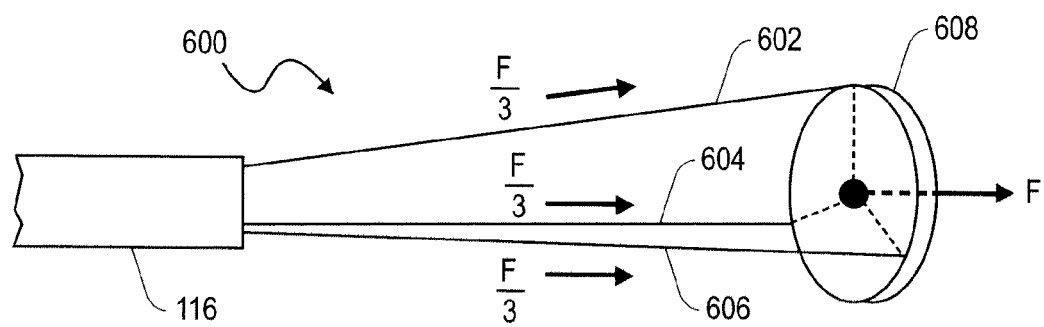
FIG. 14 illustrates an embodiment of a tendon system having more than two tendons or tendon sections.

The configuration of FIG. 14 may be extended to any number of tendons or tendon sections (2 or greater), as long as distance (D) and angle φ continue to be held equal for each tendon (or tendon section). In some embodiments, more complex pneumatic and/or spring-based systems, elements like element 608, gears, bearings, levers and/or pulleys, as well as combinations of these elements, may also be used. In such a configuration, these elements may provide a fulcrum about which the tendons may adjust their relative lengths to balance the moment.

As previously discussed, in some embodiments, the tension forces caused by angle α (not shown) of tendons 602, 604, 606 as they exit shaft 116 may need to be accounted for in determining forces acting on tendons 602, 604, 606. Although these additional tension forces may be small because the angles are small, the forces need to be accounted for in a precise system. Guides, pulleys, and/or other devices may be added to control angle α so that the additional forces on the tendons approach zero.

FIGS. 17 through 20 illustrate different deflection configurations of tendon deflection systems to provide various orientations of the shaft tip relative to the inner surface of the left ventricle of a human heart. It can be seen that the tendon deflection system may provide a large number of possible orientations without causing whipping.

Figure 17:
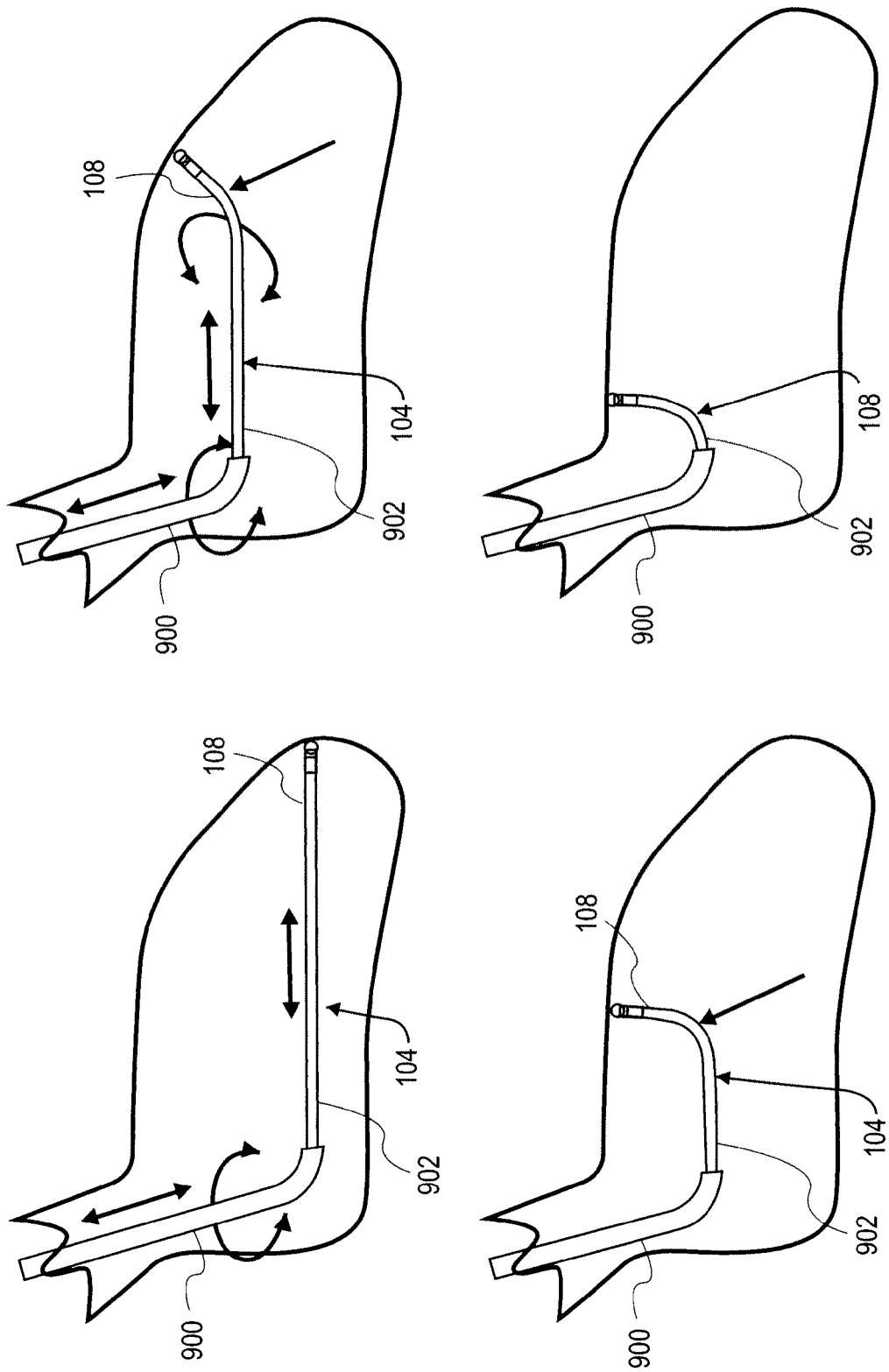
FIGS. 17 through 20 illustrate different deflection configurations of the tendon deflection system to provide various orientations for the shaft tip in a heart.
Figure 18:
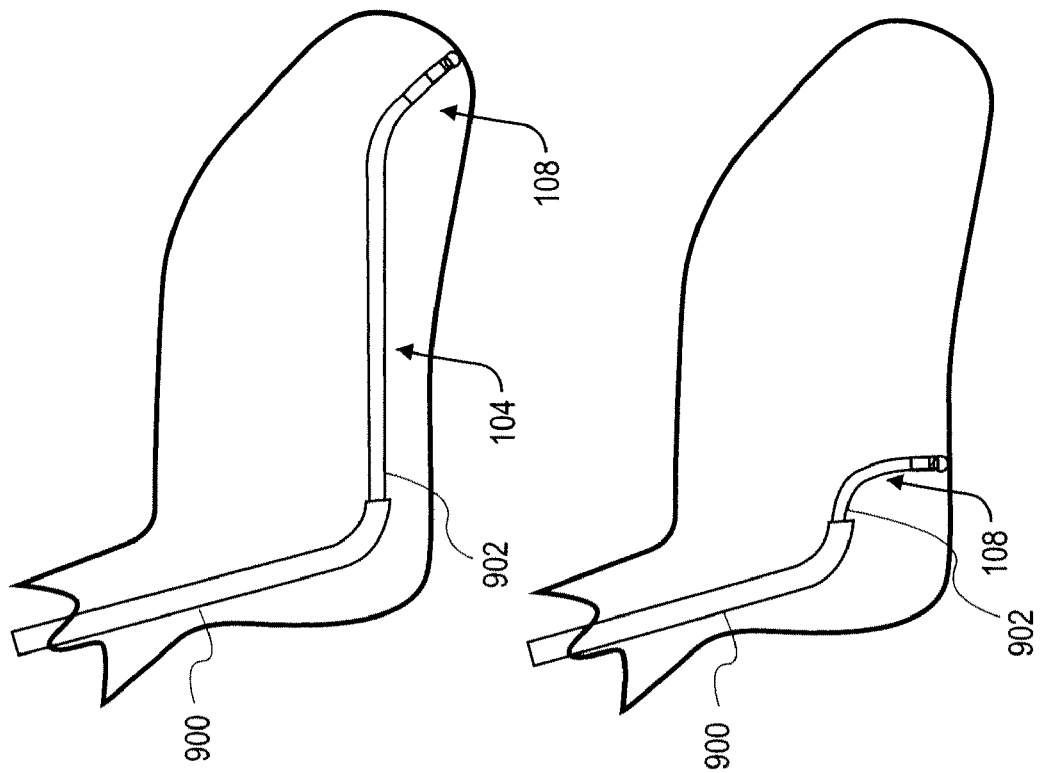
Figure 18:
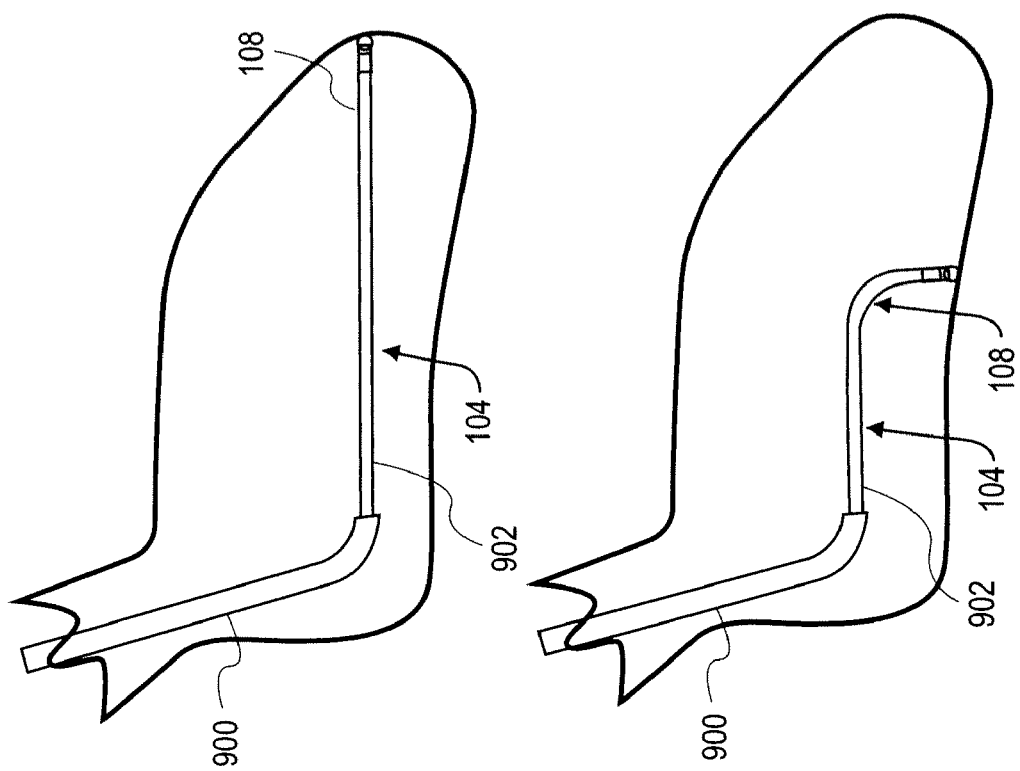

FIGS. 17 and 18 show an embodiment having fixed curve guide catheter 900 with deflectable needle catheter 902 extending therefrom. Deflectable needle catheter 902 includes sections having tendon configurations similar to sections 104 and 108 from FIG. 1.

Figure 19:
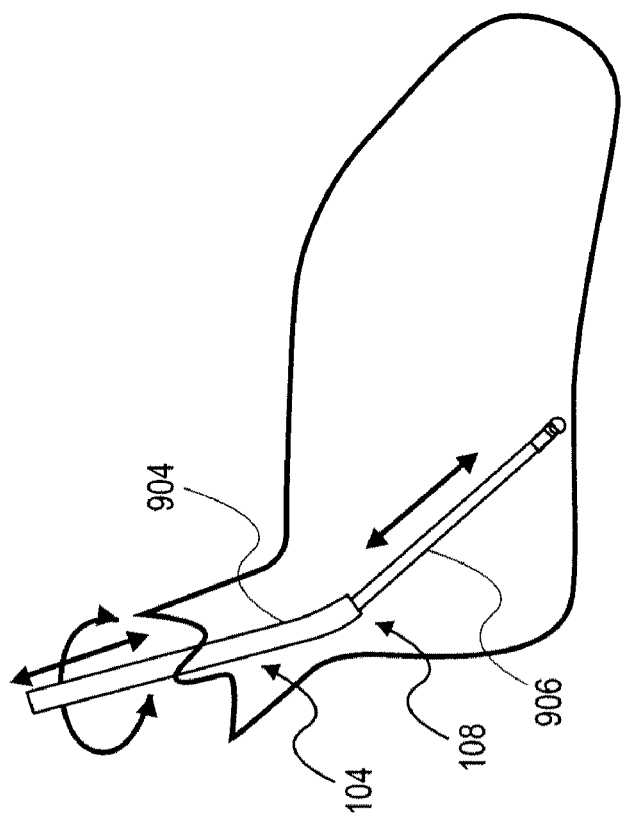
Figure 19:
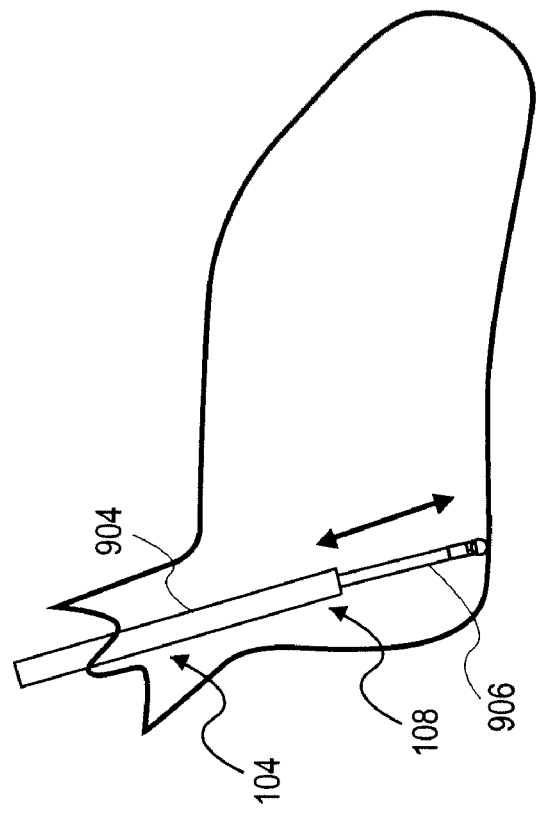
Figure 20:
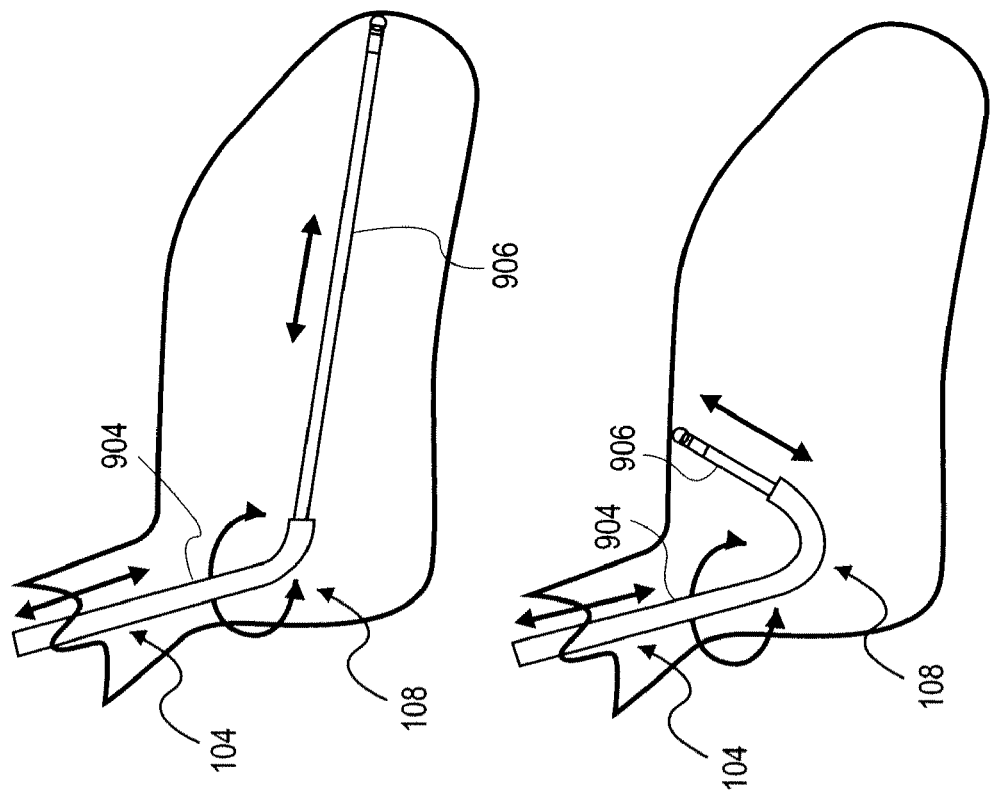
Figure 20:
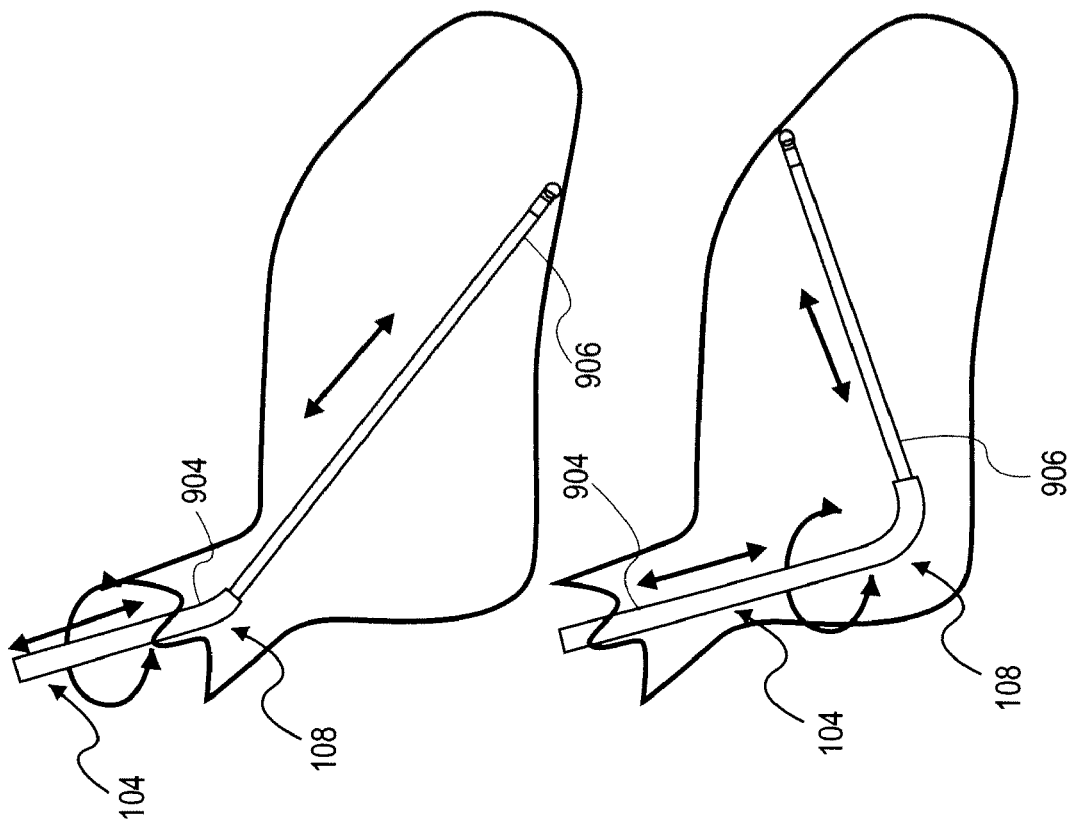

FIGS. 19 and 20 show an embodiment having deflectable guide catheter 904 with non-deflecting needle catheter 906 extending therefrom. Deflectable guide catheter 904 includes sections having tendon configurations similar to sections 104 and 108 from FIG. 1.

Figure 21:
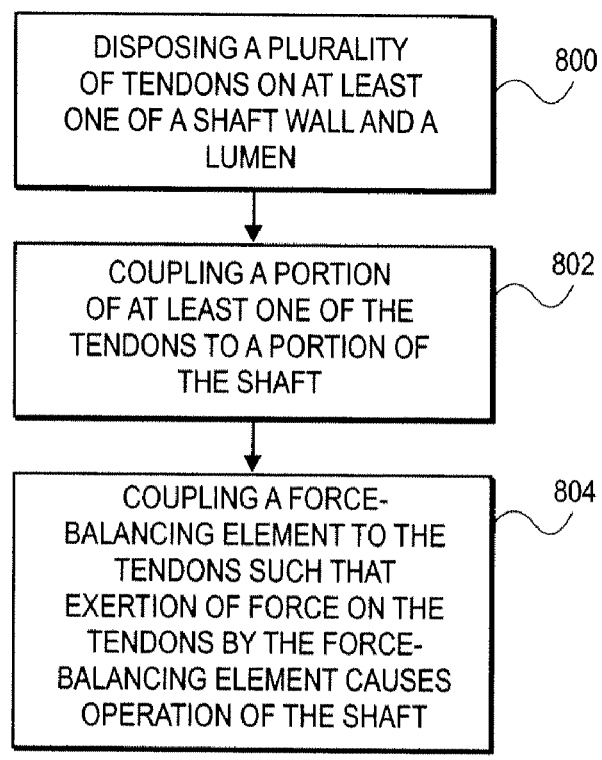
FIG. 21 is a flow chart for a method of constructing a tendon deflection system.

A method for constructing a tendon deflection system is illustrated in FIG. 21. The method includes disposing a plurality of tendons on at least one of a wall and a lumen of a first portion of a shaft, at block 800. In various embodiments, disposing tendons "on the shaft wall" refers to disposing the tendons on an outer surface of the shaft wall or within the shaft wall or both. Regardless of the tendon placement, the tendons are movable relative to the shaft. At block 802, a distal portion of at least one of the plurality of tendons is coupled to a portion of the shaft. At block 804, a force-balancing element is coupled to the plurality of tendons such that exertion of force on the tendons by the force-balancing element causes operation of the shaft.

The method can further include arranging the tendons around the shaft at an equal angle from each other and at an equal distance from the center of the shaft in order to minimize the resultant moment experienced by the proximal portion of the shaft. Thus, the tendons operate in concert with the force-balancing element to substantially eliminate deflection of the proximal portion of the shaft.

In various embodiments, operation of the shaft includes deflecting a portion of the shaft. This deflection is facilitated by disposing the tendon(s) coupled to the shaft along one side of a deflectable portion of the shaft such that the bending moment of the deflectable portion is significantly greater than the bending moment of the proximal portion of the shaft.

In other embodiments, the method further includes attaching a work device to the shaft, wherein operation of the shaft comprises actuating the work device. As described previously, the work device may be any tool, surgical device, or the like that can be attached to the shaft and actuated by the tendon configurations described herein. Some embodiments are configured to include both deflection (possibly in multiple directions) and work device actuation.

Advantages of tendon systems 100, 130, and 600 having a plurality tendons include having a smaller cross-sectional area than that required for a conventional tendon deflection system. For example, in system 100 (see FIGS. 1 and 2) having two tendon sections, each section is subjected to only one half of the force (F) applied by the deflection mechanism. Therefore, the tendon may need only one half the cross-sectional area that would be required of a conventional tendon deflection system to apply the same moment and have the same or better elongation and failure behavior. In systems having more than two tendons or tendon sections, the cross-sections of the tendon wires may be further reduced, the force produced per unit handle translation increased, and/or other benefits gained. In some systems, these benefits may outweigh the increase in the design and manufacturing complexity. The same vector analysis, as previously introduced, may be used to derive the expressed (resultant) moment amplitude and direction with any number of tendons or tendon sections.

Other advantages of having multiple tendons or tendon sections include less need to spiral the tendon wire because the expressed moment may be minimized (i.e., zero or close to zero moment). Furthermore, tight spirals may be avoided and more flexible shaft construction/materials, with much less resultant whipping, may be employed in sections of the system where the shaft is expected to be confined in a curved body lumen during use. A gentle spiraling (relatively long pitch length) of the tendon sheaths may still be desirable to minimize the effects of any uncanceled moments or shaft non-uniformities.

For example, although the embodiments show the tendon sheaths, in section 104, traveling along the shaft in a fixed and constant angle relative to each other and to the shaft, the angles of the tendon sheaths may be configured to vary relative to the shaft, but remain fixed and constant relative to each other along the length of section 104. Thus, the tendon sheaths would spiral around the shaft. Regardless of the number of tendons spiraled around the shaft, the direction of the tendon spiral can be reversed along a portion of the shaft to minimize net shaft rotation in response to the torque produced by the spiraled tendons under tension.

Such a spiral, having a cross-section similar to FIG. 7, may be constructed and, thus, exhibit small applied (expressed or resultant) moment. This spiral may also be used to guide tendon sections 112a and 112b into position, such that the applied (expressed or resultant) moment in the second catheter section of the tendon deflection system 100 may be applied in the desired direction. Accordingly, the relative magnitude of the expressed moment and the direction of the deflection may both be under design control. Also, as previously discussed, the spiral direction may be manipulated to minimize tip rotation during deflection.

Further, tendon deflection systems 100, 600 may be designed such that different sections of shaft 116 deflect in different directions with different relative magnitudes, all under a single control. When this means of controlling deflection is combined with the methods of adjusting flexural modulus of the shaft 116 and of controlling the translation of the proximal end of tendon wire 112, a larger design space may be realized to optimize or choose the design characteristics of systems 100, 600 to fit the design constraints.

One negative impact of having multiple tendons or tendon sections is having to provide a minimum of two tendon sheaths that are required to minimize or adjust the applied moment. However, the extra space required for the multiple sheaths in the shaft wall may be minimized by the reduced cross-sectional area needed for tendon 112. Since each tendon (or tendon section) experiences one half or less of the tension force required to produce the same moment in a single tendon design, it may have one half or less of the cross-sectional area and still exhibit the same failure and elongation characteristics. The space may be reduced further by the use of flat wires as tendons. Furthermore, considering the size impact of a spiraled single tendon with twice (or more) the cross-section and the desire to provide a circular shaft cross-section for sealing (hemostasis), radial symmetry and trauma reduction purposes, it may be seen that using more than one tendon (or tendon section) may actually result in a catheter size reduction.

There has been disclosed herein embodiments for controlling the degree and direction of expression of the moment created by a tendon deflection system along the length of a shaft. This tendon deflection system includes at least a first catheter section and a second catheter section. In the first catheter section where no deflection is desired (e.g., section 104 in FIGS. 1 and 2), the expressed moment is designed to be low by configuring the section with a plurality of tendons or tendon sections. In the second catheter section where deflection is desired (e.g., section 108 in FIGS. 1 and 2), the expressed moment is designed to be higher than the first catheter section to provide needed curvature.

It will also be apparent to one skilled in the art, the methods and embodiments presented may be used to create less preferred deflection systems, work device actuation systems and shaft sections that minimize the expressed moment, but do not minimize other whipping effect sources. For instance, gears, pulleys, bearings, levers and/or discs may be arranged such that they provide a controlled tendon tension force distribution, not a force balance. In such a tendon system, the expressed moment along a section of the shaft may still be minimized near zero, but the angles of the axially arranged tendons around that shaft section may not be equal.

It is to be understood that even though numerous characteristics and advantages of various embodiments have been set forth in the foregoing description, together with details of structure and function of the various embodiments, this disclosure is illustrative only. Changes may be made in detail, especially matters of structure and management of parts, without departing from the scope of the various embodiments as expressed by the broad general meaning of the terms of the appended claims.

We claim:

1. An apparatus, comprising:
a shaft having a wall and a lumen defined by the shaft;
a tendon sheath disposed on at least one of the shaft or within the shaft wherein the tendon sheath extends from a proximal portion of the shaft to a distal portion of the shaft, the tendon sheath comprising at least first and second tubular components spaced apart from one another on opposite sides of the shaft and approximately 180 degrees from each other at a proximal portion of the tendon sheath, and a third tubular component at a distal portion of the tendon sheath;
a pair of tendons movably disposed within the tendon sheath,
wherein proximal portions of respective ones of the pair of tendons are disposed in the first tubular component and the second tubular component,
wherein one of either distal portions of the pair of tendons are disposed in the third tubular component, or the pair of tendons are coupled together to a single tendon and the single tendon is disposed in the third tubular component,
wherein the third tubular component is on a side of the shaft and has a different longitudinal axis than a longitudinal axis of each of the first tubular component and the second tubular component,
an anchor member coupled to the distal portion of the shaft,
wherein one of either the distal portions of the pair of tendons are coupled to the anchor member at approximately a same location on the anchor member, or the third tendon is coupled to the anchor member; and
a force-balancing element coupled to the pair of tendons, the force-balancing element to balance a force between the pair of tendons when the distal portion of the shaft is deflected from a first position to a different second position.

2. The apparatus of claim 1, wherein, along the proximal portion of the shaft, the tendons are arranged around the shaft at an equal angle from each other and at an equal distance from a center of the shaft, such that a resultant moment experienced by the proximal portion of the shaft is minimized.

3. The apparatus of claim 2, wherein in an intermediate portion of the shaft, at least two of the tendons from the proximal portion are coupled together to form the single tendon that extends into the third tubular component, such that a resultant moment experienced by the distal portion when force is applied to the single tendon causes the distal portion to deflect.

4. The apparatus of claim 2, wherein in an intermediate portion of the shaft, at least two of the tendons from the proximal portion are disposed adjacent to each other, wherein the two adjacent tendons extend into the third tubular component, such that a resultant moment experienced by the distal portion when force is applied to the adjacent tendons causes the distal portion to deflect.

5. The apparatus of claim 1, further comprising:
a tip coupled to the distal portion of the shaft, the tip having at least one of a protrusion extending from a main body portion of the tip and a channel formed in the main body portion, such that a loop of a tendon can be coupled to the tip by engaging at least one of the protrusion and the channel; and
a holding element to engage the tip and the tendon coupled to the tip to prevent the loop from disengaging from the main body portion.

6. The apparatus of claim 5, wherein the holding element comprises:
a ring disposed around the tip such that at least a portion of the tendon coupled to the tip is disposed between the ring and the tip.

7. The apparatus of claim 1, further comprising:
a tip coupled to the distal portion of the shaft, the tip having at least one barb extending radially from a main body portion of the tip; and
a holding element to capture a portion of a tendon between the barbs of the tip and an inner surface of the holding element.

8. The apparatus of claim 7, wherein the holding element comprises:
   a ring.

9. The apparatus of claim 1, wherein the tendons comprise:
   a tendon disposed on at least one of an outer surface of the shaft wall and within the shaft wall.

10. The apparatus of claim 1, wherein the force-balancing element comprises:
    a pulley coupled to at least one of a loop and an end of each of the tendons coupled to the pulley.

11. The apparatus of claim 1, wherein the force-balancing element comprises:
    a disc coupled to at least one of a loop and an end of each of the tendons coupled to the disc.

12. The apparatus of claim 1, further comprises:
    a work device coupled to a distal end of the shaft and to at least one of the tendons such that force exerted on the force-balancing element actuates the work device.

13. The apparatus of claim 1, wherein in an intermediate portion of the shaft between the proximal portion and the distal portion, in response to a defection of the distal portion a resultant moment vector applied to the intermediate portion is zero.

14. The apparatus of claim 1, wherein one of either the distal portions of the pair of tendons are coupled to the anchor member on a same side of the shaft, or the third tendon is coupled to the anchor member on one side of the shaft.

* * * * *

UNITED STATES PATENT AND TRADEMARK OFFICE
CERTIFICATE OF CORRECTION

PATENT NO. : 7,594,903 B2
APPLICATION NO. : 10/255034
DATED : September 29, 2009
INVENTOR(S) : Webler et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this

Twenty-eighth Day of September, 2010

David J. Kappos
*Director of the United States Patent and Trademark Office*